United States Patent
Bongers et al.

Patent Number: 4,692,521
Date of Patent: Sep. 8, 1987

[54] N-SUBSTITUTED ACYL-LACTAM COMPOUND

[75] Inventors: Jozef J. M. Bongers, Elsloo; Albert A. Van Geenen, Brunssum, both of Netherlands

[73] Assignee: Stamicarbon B.V., Geleen, Netherlands

[21] Appl. No.: 808,558

[22] Filed: Dec. 13, 1985

[30] Foreign Application Priority Data

Dec. 20, 1984 [NL] Netherlands ................. 8403861

[51] Int. Cl.$^4$ ............................. C07D 223/10
[52] U.S. Cl. ............................. 540/451; 546/221; 546/243; 548/538; 548/540; 525/315; 540/529
[58] Field of Search ............... 260/239.3 R; 546/243, 546/221; 548/538, 540; 540/531, 529, 451

[56] References Cited

U.S. PATENT DOCUMENTS

| | | | |
|---|---|---|---|
| 3,366,608 | 1/1968 | Lincoln et al. | 540/525 |
| 3,451,963 | 6/1969 | Tierney et al. | 540/486 |
| 3,875,147 | 4/1975 | Choi | 548/538 |
| 4,031,164 | 6/1977 | Hedrick et al. | 540/525 |
| 4,590,243 | 5/1986 | Gabbert et al. | 525/184 |
| 4,626,385 | 12/1986 | Ashida et al. | 540/451 |

Primary Examiner—Robert T. Bond
Attorney, Agent, or Firm—Cushman, Darby & Cushman

[57] ABSTRACT

The invention relates to N-substitutecd acyl lactam compounds of the formula

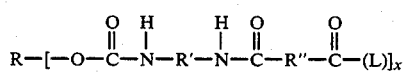

where
 R is a polyol residue originating from a polyol with the formula $R\text{-}(OH)_x$ where x is a number $\leq 2$
 R' a bivalent cyclic or non-cyclic alkyl, aralkyl, alkaryl or aryl radical
 R'' a bivalent radical having the following general formula

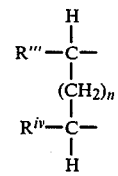

wherein
 R''' is H, alkyl, cycloalkyl, aryl, alkaryl or aralkyl,
 R$^{iv}$ is H, alkyl, cycloalkyl, aryl, alkaryl or aralkyl where
 R''' and R$^{iv}$ may jointly form a substituted or non-substituted cycloalkyl residue
 n is 0 or 1 and
 (-L) represents a non-opened lactam ring of the formula

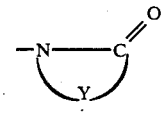

wherein Y is hydrocarbon residue with 3–11 carbon atoms.

It has been found that this group of compounds is very suitable as activator in the preparation of nylon block copolymers, more specifically in the RIM or RRIM systems.

11 Claims, No Drawings

N-SUBSTITUTED ACYL-LACTAM COMPOUND

FIELD OF THE INVENTION

The invention relates to an N-substituted acyl-lactam compound. In the anionic polymerization of lactams, such as caprolactam, N-substituted acyl-lactam compounds are suitable accelerators. These compounds can be used particularly in the preparation of RIM (=Reaction Injection Moulding) nylon on account of the short time required for their reaction, which makes it possible for lactam to be polymerized in a mould.

BACKGROUND OF THE PRESENT INVENTION

The RIM preparation process is a one-step process in which the liquid components are put in a mould, upon which a very rapid polymerization takes place resulting in a plastic article. The pressures applied in that process are much lower than in the much used injection moulding process.

In a RIM preparation process the viscosity of the components put in the moulds is 50 to 10,000 cps, preferably about 1000-3000 cps. In that process the temperature of the components ranges from room temperature for urethanes to about 100°-150° C. for lactams. The mould temperature in a RIM preparation processs for lactams is usually between 100° and 220° C. The pressures applied range from 1 to 100 bar, preferably from 1 to 30 bar.

For smaller articles the reaction in the mould must be finished in less than 5 minutes.

The polymerization of a lactam to form nylon has been known for long.

In the U.S. Pat. No. 3,018,273 a process for the anionic polymerization of caprolactam is described using an organomagnesium compound as catalyst and an N-N diacyl compound as activator.

The British Pat. No. 1,067,153 describes a process for preparing nylon block copolymers by polymerizing caprolactam in the presence of various kinds of activators. In the example the use of an isocyanate-terminated polypropylene glycol as activator and of a potassium compound as catalyst is described.

In the U.S. Pat. Nos. 3,862,262, 4,031,164, 4,034,015, 4,223,112, 3,925,325 and 3,965,075, as well as Reissue U.S. Pat. No. Re. 30,371, various aspects of the preparation of activators for the polymerization of lactam and of the polymerization of lactam itself are described.

The U.S. Pat. Nos. 4,031,164 and 4,223,112 describe lactam-polyol-polyacyl-lactam block copolymers with specific ratios of the various components.

The U.S. Pat. No. 3,862,262 describes lactam-polyol-acyl-polylactam block copolymers.

The U.S. Pat. No. 4,034,015 aims at nylon block copolymers with at least 5% ester end groups.

The other patents mentioned relate to the preparation of ester-amide compounds by condensation of alcohol and acyl-lactam in the presence of various kinds of catalysts.

The European patent applications Nos. 67693, 67694 and 67695 laid open to public inspection relate to acyl-halide and acyl-lactam compounds and to a process for preparing nylon block copolymers with these. The acyl-halide and acyl-lactam compounds are described by means of complex formulas.

The U.S. Pat. No. 3,366,608 describes the reaction of an N,N'diacyl-bis caprolactam, such as N,N'sebacoyl-bis-caprolactam, a polyol and a basic catalyst. In that process a nylon block copolymer is obtained.

The German patent application no. 2026672 laid open to public inspection describes the use of polyol-containing polyamides for the production of metallized articles. The polyol-containing polyamides are obtained by anionic polymerization of lactam in the presence of a polyol, a basic lactam catalyst and an activator, such as a diisocyanate.

The U.S. Pat. No. 4,540,516 describes the preparation of N-substituted carbamoyl-lactam compounds, while the U.S. Pat. No. 4,540,515 describes the use of such a compound for the preparation of nylon block copolymers.

The European patent application no. 147792 describes the catalytic condensation of imides and alcohols to form esteracyl-lactam and esteramide-acyl-lactam compounds.

In the U.S. Pat. No. 3,704,280 a process is described for the anionic catalytic polymerization of lactam in the presence of a polyether, in which process the activator used is an isocyanate compound.

SUMMARY OBJECTS OF THE PRESENT INVENTION

The invention relates to N-substituted acyl lactam compounds of the formula

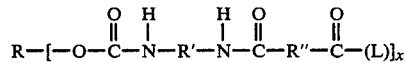

where
R is the residue originating from a polyol having the formula R—(OH)$_x$ where x is a number $\geq 2$;
R' is a bivalent cyclic or non-cyclic alkyl, aralkyl, alkaryl or aryl radical;
R" is a bivalent radical having the following general formula

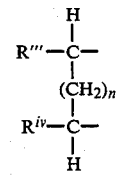

wherein
R'" is H, alkyl, cycloalkyl, aryl, alkaryl or aralkyl,
R$^{iv}$ is H, alkyl, cycloalkyl, aryl, alkaryl or aralkyl, where
R'" and R$^{iv}$ may, together with the carbon atom to which each is respectively bonded, jointly form a substituted or un-substituted cycloalkyl residue;
n is 0 or 1; and
(-L) represents un-opened lactam ring having the formula

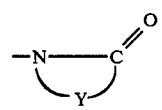

wherein Y has 3-11 carbon atoms.

These compounds are very suitable for use as activators in the preparation of nylon block copolymers, and more specifically in RIM or RRIM systems.

The present invention provides a novel N-substituted acyl-lactam compound that can well be used, inter alia, as accelerator for anionic polymerization of lactam as may be applied, for instance, in (rotational) moulding of nylon.

The present invention also provides a novel N-substituted acyl-lactam compound capable of producing nylon block copolymers with good properties, particularly via 'Reaction Injection Moulding'.

DETAILED DESCRIPTION OF THE PRESENT INVENTION

The N-substituted acyl-lactam compound according to the invention is characterized by the formula:

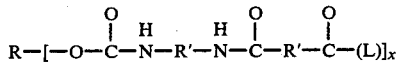

where:
R is a polyol residue originating from a polyol with the formula $R-(OH)_x$ where x is a number $\geq 2$
R' a bivalent cyclic or non-cyclic alkyl, aralkyl, alkaryl or aryl radical
R" a bivalent radical having the following general formula:

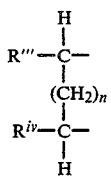

wherein
R''' is H, alkyl, cycloalkyl, aryl, alkaryl or aralkyl,
$R^{iv}$ is H, alkyl, cycloalkyl, aryl, alkaryl or aralkyl where
R''' and $R^{iv}$ may jointly form a substituted or non-substituted cycloalkyl residue
n is 0 or 1, and
(-L) represents a non-opened lactam ring of the formula

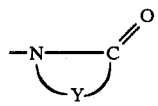

wherein Y is a hydrocarbon residue with 3–11 carbon atoms.

It has been found that this group of compounds is very suitable as activator in the preparation of nylon block copolymers, more specifically in the so-called RIM (Reaction Injection Moulding) or RRIM (reinforced RIM) systems, in which it is highly essential for the polymerization to take effect within a very short time.

Moreover, using these compounds highly impact-resistant articles can be made from nylon block copolymers.

The compounds according to the invention can be prepared by reacting the reaction product of a lactam with a dicarboxylic acid anhydride in liquid state at a temperature of at most 150° C. with the reaction product of a polyol with a polyisocyanate, which latter reaction product contains isocyanate groups. Preferably a temperature between 30° C. and 140° C. is applied and more preferably between 50° C. and 130° C. Liquid state is understood to mean a mixture of two liquids as well as a solid component dissolved in a liquid component.

The reaction product (I) of a lactam with a dicarboxylic acid anhydride is understood to comprise compounds with the formula:

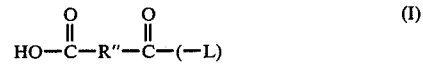

where
R" is a bivalent radical having the following general formula

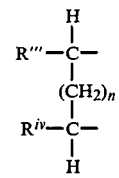

wherein
R''' is H, alkyl, cycloalkyl, aryl, alkaryl or aralkyl,
$R^{iv}$ is H, alkyl, cycloalkyl, aryl, alkaryl or aralkyl where
R''' and $R^{iv}$ may jointly form a substituted or non-substituted cycloalkyl residue
n is 0 or 1 and
(-L) represents a non-opened lactam ring of the formula

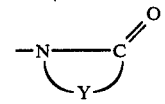

wherein Y is a hydrocarbon residue with 3–11 carbon atoms.

This reaction product (I) is formed when a dicarboxylic acid anhydride and a lactam are reacted with each other in a liquid state at a temperature of 150° C. at most. Preferably at a temperature between 70° C. and 140° C. and more preferably between 90° C. and 130° C.

The reaction product (II) of a polyol with a polyisocyanate, containing isocyanate groups, may be understood to comprise compounds having the formula

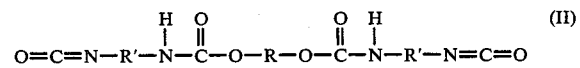

where:
R is a polyol residue originating from a polyol with the formula $R-(OH)_x$, where x is a number $\geq 2$
R' is a bivalent cyclic or non-cyclic alkyl, aralkyl, alkaryl or aryl radical.

This reaction product (II) is formed when a polyol and polyisocyanate are reacted with each other at a temperature of 150° C. at most, preferably between 20° C. and 140° C. and more preferably between 40° C. and 120° C.

If reaction product (I) and reaction product (II) are brought together, the N-substituted acyl-lactam compounds according to the present invention will be formed while carbon dioxide is being separated off. The temperature of the reaction between reaction product (I) and reaction product (II) is 150° C. at most and preferably between 30° C. and 140° C.

The polyol applied may in principle be any polyol, but on the grounds of the mechanical properties to be obtained preference is given to rubber-like polyols with an equivalent weight of at least 300, more specifically from 1000 to 5000. Beyond an equivalent weight of 5000 the properties of the nylon block copolymer may deteriorate.

Suitable polyols are polyether polyols, polyester polyols, polybutadiene polyols, siloxane-containing polyols and/or the so-called 'polymeric' polyols. These 'polymeric' polyols comprise polyols grafted with, for instance, acrylonitrile or a mixture of styrene and acrylonitrile, but also the polyurea dispersions obtained by reacting equivalent amounts of diamine or hydrazine with diisocyanate dissolved in the polyol.

The concepts of molecular weight and equivalent weight as used herein relate to the number-average molecular weight.

The concept of equivalent weight of a polyol relates to the number-average molecular weight of the polyol per hydroxyl group, i.e. the molecular weight divided by the functionality.

Mixtures of two or more polyols may be started from also.

Various polyisocyanates are suitable for use in the present invention. These may be aliphatic, araliphatic, cycloaliphatic and aromatic isocyanates.

Examples of suitable isocyanates are 1,5-hexanediisocyanate, 1,6-hexanediisocyanate, xylylenediisocyanate (XDI), isophoronediisocyanate, toluenediisocyanate (TDI), 4,4'-diphenylmethanediisocyanate (MDI) and hydrogenated TDI, XDI or MDI, modified MDI (e.g. with carbodiimide).

As lactam various lactams may be used, such as 2-pyrrolidone, 2-piperidone, enantholactam, decanolactam, undecanolactam, lauryllactam and caprolactam, but also substituted lactams, or mixtures of two or more lactams.

More specifically caprolactam is used.

The dicarboxylic acid anhydrides to be used as chosen from the group of dicarboxylic acid anhydrides having the following general formula:

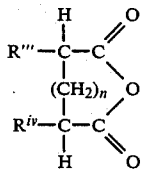

where:
R''' represents H, alkyl, cycloalkyl, aryl, alkaryl or aralkyl
$R^{iv}$ is H, alkyl, cycloalkyl, aryl, alkaryl or aralkyl where R''' and $R^{iv}$ may jointly form a substituted or non-substituted cycloalkyl residue, and
n is 0 or 1.

Very suitable are dicarboxylic acid anhydrides, such as glutaric acid anhydride, succinic acid anhydride, and saturated alicyclic 1,2 dicarboxylic anhydrides, such as 1,2 cyclohexanedicarboxylic acid anhydride.

Applicant has found that compounds like maleic acid anhydride and phthalic acid anhydride cannot be used in the present invention.

The present invention also relates to a process for preparing a nylon block copolymer, as well as to an article wholly or partly produced from such a nylon block copolymer.

This process is characterized in that an N-substituted acyl-lactam compound described above is reacted in melted lactam to form a nylon block copolymer in the presence of a lactam polymerization catalyst. Preference is given to carrying out the reaction with an alkali or alkaline earth metal lactamate or with compounds forming alkali or alkaline earth metal lactamate. Examples thereof include potassium lactamate and lactam magnesiumbromide. Already a small amount of catalyst will suffice, for instance less than 1 mole % calculated on the lactam to be polymerized, but larger amounts, to for instance 3 moles % can also be used. Preferably the amount of catalyst is between 0.2 and 3 moles %.

The block copolymer is formed in a short time, for instance in less than 10 minutes, more specifically between 10 and 5 minutes, under mild conditions in respect of temperature and pressure.

The proportions between lactam monomer and acyl-lactam may vary within wide limits. These proportions are generally between 5 and 99% (wt) of each of the components. In order to obtain suitable impact-resistant articles having a reasonable hardness and rigidity preference is given to 5-40% (wt) acyl-lactam compound calculated on the total mixture. More specifically 10-30% (wt) acyl-lactam compound is used.

In the preparation of nylon block copolymer the object is for the number-average molecular weight of the nylon blocks to be at least 2000, more specifically at least 4000. This can be achieved by varying the number of acyl-lactam groups originating from the acyl-lactam compound in respect of the amount of lactam added.

The chosen lactam added for preparing the nylon block copolymer is preferably the same as used in the acyl-lactam compound. More specifically caprolactam is used.

In the preparation of the nylon block copolymer it may be essential for the polymerization to be carried out in the presence of one or more compounds that are normally used in nylon block copolymers, such as fillers, softeners, flame-retardants, stabilizers and reinforcing fibres, such as asbestos or glass fibres.

The present invention is elucidated hereinafter by means of a few examples.

EXAMPLE 1

28.5 g (0.25 mole) glutaric acid anhydride and 28.25 g (0.25 mole) ε-caprolactam were reacted for 4 hours at 125° C.

Subsequently, to the reaction product formed 542 g isocyanate-terminated polypropyleneglycol prepolymer (reaction product of 0.125 mole PPG 4000 and 0.25 mole hexamethylenediisocyanate) was added gradually at 110° C. Immediately after addition $CO_2$ formation was observed. After complete addition (2 hours) the whole was after-reacted under vacuum for 1 hour at 125° C. I.R. analysis showed that the lactam rings were intact.

EXAMPLE 2

25 g (0.25 mole) succinic acid anhydride and 28.25 g (0.25 mole) ε-caprolactam were reacted for 4 hours at 125° C. Subsequently, to the reaction product formed 555.5 g isocyanate-terminated polypropyleneglycol prepolymer (reaction product of 0.125 mole PPG 4000 and 0.25 mole isophoronediisocyanate) was added gradually at 110° C. After complete addition (2 hours) the whole was after-reacted under vacuum for 1 hour at 125° C.

11.7 g of the product formed was dissolved in 13 g caprolactam at 100° C. After addition of this solution to 0.5 g lactam-magnesiumbromide in 14.7 g caprolactam a solid nylon polymer was formed herefrom at 130° C. in 4 min. and 30 sec.

EXAMPLE 3

38.5 g (0.25 mole) 1.2 cyclohexanedicarboxylic acid anhydride and 28.25 g (0.25 mole) ε-caprolactam were reacted for 4 hours at 125° C. Subsequently, to the reaction product formed, 542 g isocyanate-terminated polypropyleneglycol prepolymer (reaction product of 0.125 mole PPG 4000 and 0.25 mole hexamethylenediisocyanate) was added gradually at 110° C. After complete addition (2 hours) the whole was after-reacted under vacuum for 1 hours at 125° C. 15 g of the product formed was dissolved in 20 g caprolactam at 100° C. After addition of this solution to 0.4 g potassiumlactamate in 16.1 g caprolactam a solid nylon polymer was formed herefrom at 130° C. in 3 min. and 45 sec.

We claim:

1. N-substituted acyl-lactam compound, characterized by the formula:

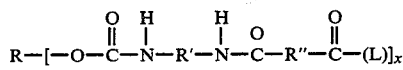

where
R is a residue originating from a polyol having the formula R—(OH)$_x$ where x is a number $\geq 2$ and having an equivalent weight of at least 300 and up to 5,000;
R' a bivalent cyclic or non-cyclic alkyl, aralkyl, alkaryl or aryl radical;
R" a bivalent radical residue from a dicarboxylic acid, anhydride having the following formula

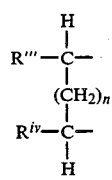

wherein
R''' is H, alkyl, cycloalkyl, aryl, alkaryl or aralkyl,
R$^{iv}$ is H, alkyl, cycloalkyl, aryl, alkaryl or aralkyl, where
R''' and R$^{iv}$ may jointly, together with the carbon atom to which is respectively bonded, form a substituted or un-substituted cycloalkyl residue;
n is 0 or 1; and
(-L) represents a non-opened lactam ring of the formula

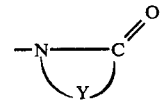

wherein Y has 3-11 carbon atoms.

2. The compound according to claim 1, wherein R' is the bivalent radical residue of 1,5-hexanediisocyanate, 1,6-hexanediisocyanate, isophoronediisocyanate, toluenediisocyanate, MDI, hydrogenated MDI, modified MDI and xylylenediisocyanate.

3. The compound according to claim 1, wherein R is a residue of a polyether polyol, polyester polyol, a polybutadiene polyol, a siloxane-containing polyol(s), polymeric polyol(s) or mixtures thereof.

4. The compound according to claim 1, wherein R" is the bivalent radical residue of glutaric acid anhydride, succinic acid anhydride or 1,2 cyclohexanedicarboxylic acid anhydride.

5. The compound according to claim 1 wherein:
R' is the bivalent radical residue of 1,5-hexane diisocyanate, 1,6 hexanediisocyanate, isophoronediisocyanate, toluenediisocyanate, MDI, hydrogenated MDI, modified MDI, xylylenediisocyanate and hydrogenated toluenediisocyanate;
R is a residue of a polyether polyol, a polyester polyol, a polybutadiene polyol, a siloxane-containing polyol(s), polymeric polyol(s), or mixtures thereof;
R" is the bivalent radical residue of a dicarboxylic acid anhydride selected from the group consisting of glutaric acid anhydride, succinic acid anhydride, or 1,2 cyclohexane dicarboxylic acid anhydride; and
L represents a lactam ring wherein the lactam of said lactam ring is selected from the group consisting of 2-pyrrolidone, 2-piperidone, enantholactam, decanolactam, undecanalactam, lauryll lactam, caprolactam and mixtures thereof.

6. A process for preparing an N-substituted acyl lactam compound comprising:
reacting a 4–12 carbon atom lactam with a dicarboxylic anhydride in the liquid state at a temperature of at most 150° C. whereby a reaction product(s) is obtained;
reacting the thus obtained reaction product(s) with the separate reaction product of a polyol having an equivalent weight of at least 300 up to 5,000 with a diisocyanate selected from the group consisting of 1,5-hexanediisocyanate, 1,6-hexanediisocyanate, xylylenediisocyanate, isophoronediisocyanate, toluenediisocyanate, diphenylmethanediisocyanate, hydrogenated toluenediisocyanate, hydrogenated, xylylenediisocyanate, hydrogenated 4,4'diphenylmethanediisocyanate, and modified 4,4'diphenylmethanediisocyanate,
whereby the N-substitute acyl-lactam compound is formed, and subsequently recovered.

7. The process according to claim 6 wherein the polyol equivalent weight ranges from 1,000–5,000.

8. The process according to claim 6 wherein said lactam and said dicarboxylic anhydride are reacted at a temperature ranging between 70° C. and 140° C.

9. The process according to claim 8 wherein the polyol and the polyisocyanate are reacted at a temperature ranging from 20° C. to 140° C.

10. The process according to claim 6 wherein the reaction product of said lactam and said dicarboxylic anhydride and the reaction product of said polyol and said polyisocyanate are reacted together at a temperature from about 30° C. to 140° C.

11. The process according to claim 6 wherein said process:

said lactam and said dicarboxylic acid anhydride are reacted at a temperature ranging from 70° C. to 140° C.;

said lactam is selected from the group consisting of 2-pyrrolidone, 2-piperidone, enantholactam, decanolactam, undecanolactam, lauryllactam and caprolactam and mixtures thereof;

said acid anhydride is selected from the group consisting of glutaric acid anhydride, succinic acid anhydride and 1,2-cychlohexane dicarboxylic acid anhydride; and the reaction product of said lactam and said dicarboxylic anhydride is a reacted with the reaction product of said polyol and said polyisocyanate at a temperature ranging from 30° C. to 140° C.

* * * * *